US006890532B2

(12) United States Patent
Hooper et al.

(10) Patent No.: US 6,890,532 B2
(45) Date of Patent: May 10, 2005

(54) RABIES VIRUS-SPECIFIC NEUTRALIZING HUMAN MONOCLONAL ANTIBODIES AND NUCLEIC ACIDS AND RELATED METHODS

(75) Inventors: Douglas C. Hooper, Medford, NJ (US); Bernhard Dietzschold, Newtown Square, PA (US)

(73) Assignee: Thomas Jefferson University, Philadelphia, PA (US)

( * ) Notice: Subject to any disclaimer, the term of this patent is extended or adjusted under 35 U.S.C. 154(b) by 308 days.

(21) Appl. No.: 09/848,832

(22) Filed: May 4, 2001

(65) Prior Publication Data

US 2003/0165507 A1 Sep. 4, 2003

Related U.S. Application Data

(60) Provisional application No. 60/204,518, filed on May 16, 2000.

(51) Int. Cl.[7] .............................................. A61K 39/42
(52) U.S. Cl. ................................ 424/147.1; 424/142.1; 530/388.3; 530/388.15
(58) Field of Search ..................... 530/388.3, 388.15; 424/147.1, 142.1, 224.1; 435/252.3; 436/548, 93.2; 536/23.53

(56) References Cited

FOREIGN PATENT DOCUMENTS

| EP | 239400 | 3/1987 | ............ C12N/15/00 |
| EP | 332424 | 3/1989 | ............ C12N/15/00 |
| EP | 338745 | 3/1995 | ............ C12N/15/00 |
| WO | WO 89/09622 | 10/1989 | ......... A61K/39/395 |
| WO | WO 89/09789 | 10/1989 | ............ C07K/15/00 |
| WO | WO 93/21319 | 10/1993 | ............ C12N/15/13 |

OTHER PUBLICATIONS

Morimoto et al., "Characterization Of A Unique Variant Of Bat Rabies Virus Responsible For Newly Emerging Human Cases In North America", *Proc. Natl. Acad. Sci. USA*, vol. 93, pp. 5653–5658, (1996).

Dietzshold, B., "Techniques For The Purification Of Rabies Virus, Its Subunits And Recombinants Products," *Laboratory Techniques in Rabies*, Meslin et al., (Eds.) World Health Organization, Geneva, pp. 175–180, (1996).

Plebanski, M. et al., "Primary And Secondary Human In Vitro T–Cell Responses To Soluble Antigens Are Mediated By Subsets Bearing Different CD45 Isoforms", *Immunology*, vol. 75, pp. 86–91, (1992).

Hooper, D., "Rabies Virus", *Manual of Clinical Laboratory Immunology, Part II*, 5th ed., N.R. Rose (Ed.), ASM Press, Wash. D.C., pp. 755–760, (1997).

Pearson, W., et al., "Improved Tools For Biological Sequence Comparison", *Proc. Natl. Acad. Sci. USA*, vol. 85, pp. 2444–2448, (1988).

Champion, J.M., et al., "The Development Of Monoclonal Human Rabies Virus–Neutralizing Antibodies As A Substitute For Pooled Human Immune Globulin In The Prophylactic Treatment Of Rabies Virus Exposure", *J. Immunological Methods*, vol. 235, 81–90, (2000).

Pluckthun, A., "Antibody Engineering: Advances From The Use Of *Escherichia Coli* Expression Systems", *Bio/Technology*, vol. 9, pp. 545–551, (1991).

Dietzschold, B., et al., "Biological Characterization Of Human Monoclonal Antibodies To Rabies Virus", *J. Virol.*, vol. 64, pp. 3087–3090, (1990).

Morimoto et al., Proc. Natl. Acad. Sci. USA, 93–5653 (1996).

Dietzschold, B., "Techniques for the purification of rabies virus, its subunits and recombinants products," In: *Laboratory Techniques in Rabies*, Meslin et al., (Eds.) World Health Organization, Geneva, pp. 175–180 (1996).

Plebanski et al., Immunology, 75:86 (1992).

Hooper, D., "Rabies Virus," In: *Manual of Clinical Laboratory Immunology, Part II*, 5th ed., N.R. Rose (Ed.), ASM Press, Wash. D.C., pp. 755–760, (1997).

Pearson, et al., Proc. Natl. Acad. Sci. USA 85:2444–2448 (1988).

Champion, J.M., et al., J. Immunological Methods, 235:81–90, (2000).

Pluckthun, A., Bio/Technology 9:545–551 (1991).

Cheung, S.C., et al., J. Virol., 66:6714–6720 (1992).

Muller, B.H., et al., J. Virol. Methods, 67:221–233 (1997).

Ikematsu, H. et al., J. Immunol., 150:1325–1338 (1993).

Rando, R.F., et al., Curr. Top. Microbiol. Immunol., 187:195–205 (1994).

Dietzschold, B., et al., J. Virol., 64:3087–3090 (1990).

*Primary Examiner*—Laurie Scheiner
(74) *Attorney, Agent, or Firm*—Drinker Biddle & Reath LLP

(57) ABSTRACT

Human monoclonal rabies virus neutralizing antibodies represent a safe and efficacious post-exposure prophylactic therapy for individuals exposed to a rabies virus. The nucleic acid and encoded amino acid sequences of the heavy and light chain immunoglobulins of human monoclonal rabies virus neutralizing antibodies, and their use, is described.

3 Claims, No Drawings

SEQUENCE LISTING

<160> NUMBER OF SEQ ID NOS: 8

<210> SEQ ID NO 1
<211> LENGTH: 1430
<212> TYPE: DNA
<213> ORGANISM: Homo sapien

<400> SEQUENCE: 1

```
accatggagt ttgggctgag ctggcttttt cttgtggcta ttttaaaagg tgtccagtgt      60
gaggtgcagc tgttggagtc tgggggaggc ttggtacagc ctgggggtc cctgagactc      120 tcctgtgcag cctctggatt cacctttagc aactatgcca tgagctgggt ccgccaggct      180
ccagggaagg ggctggagtg ggtctcagct attagtgcta gtggtcatag cacatatttg      240
gcagactccg tgaagggccg gttcaccatc tccagagaca attccaagaa cacgctgtat      300
ctgcaaatga acagcctgag agccgaggac acggccgtat attactgtgc gaaagatcga      360
gaggttacta tgatagttgt acttaatgga ggctttgact actggggcca gggaacccgg      420
gtcaccgtct cctccgcctc caccaagggc ccatcggtct tccccctggc acctcctcc       480 aagagcacct ctgggggcac agcggccctg ggctgcctg tcaaggacta cttccccgaa       540
ccggtgacgg tgtcgtggaa ctcaggcgcc ctgaccagcg gcgtgcacac cttcccggct      600
gtcctacagt cctcaggact ctactccctc agcagcgtgg tgaccgtgcc ctccagcagc      660
ttgggcaccc agacctacat ctgcaacgtg aatcacaagc ccagcaacac caaggtggac      720
aagagagttg agcccaaatc ttgtgacaaa actcacacat gcccaccgtg cccagcacct      780
gaactcctgg ggggaccgtc agtcttcctc ttccccccaa acccaagga caccctcatg      840 atctcccgga cccctgaggt cacatgcgtg gtggtggacg tgagccacga agaccctgag      900
gtcaagttca actggtacgt ggacggcgtg gaggtgcata atgccaagac aaagccgcgg      960
gaggagcagt acaacagcac gtaccgtgtg gtcagcgtcc tcaccgtcct gcaccaggac      1020
tggctgaatg gcaaggagta caagtgcaag gtctccaaca aagccctccc agccccatc      1080 gagaaaacca tctccaaagc caaagggcag ccccgagaac cacaggtgta caccctgccc      1140
ccatcccggg aggagatgac caagaaccag gtcagcctga cctgcctggt caaaggcttc      1200
tatcccagcg acatcgccgt ggagtgggag agcaatgggc agccggagaa caactacaag      1260
accacgcctc ccgtgctgga ctccgacggc tccttcttcc tctatagcaa gctcaccgtg      1320
gacaagagca ggtggcagca ggggaacgtc ttctcatgct ccgtgatgca tgaggctctg      1380
cacaaccact acacgcagaa gagcctctcc ctgtccccgg gtaaatgagt                1430
```

<210> SEQ ID NO 2
<211> LENGTH: 708
<212> TYPE: DNA
<213> ORGANISM: Homo sapien

<400> SEQUENCE: 2

```
agcatggaag ccccagctca gcttctcttc ctcctgctac tctggctccc agataccacc      60
ggagaaattg tgttgacaca gtctccagcc acctgtctt tgtctccagg ggaaagagcc      120
accctcgcct gcagggccag tcagactgct agcaggtact tagcctggta ccaacagaaa      180
```

-continued

```
cctggccagg ctcccagact cctcatctat gatacatcca acagggccac tggcatccca    240
gccaggttca gtggcagtgg gtctgggaca gacttcactc tctccatcag cagcctggag    300
cctgaagatt ttgcagttta ttactgtcag cagcgtttca actggccgtg gacgttcggc    360
caagggacca aggtggaatt caaacgaact gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgttag                 708
```

```
<210> SEQ ID NO 3
<211> LENGTH: 474
<212> TYPE: PRT
<213> ORGANISM: Homo sapien

<400> SEQUENCE: 3

Met Glu Phe Gly Leu Ser Trp Leu Phe Leu Val Ala Ile Leu Lys Gly
 1               5                  10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Ala Met Ser Trp Val Arg Gln Ala Pro Gly Lys Gly Leu
    50                  55                  60

Glu Trp Val Ser Ala Ile Ser Ala Ser Gly His Ser Thr Tyr Leu Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Asp Arg Glu Val Thr Met Ile Val Val Leu Asn
        115                 120                 125

Gly Gly Phe Asp Tyr Trp Gly Gln Gly Thr Arg Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
```

```
                    275                 280                 285
Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 4
<211> LENGTH: 234
<212> TYPE: PRT
<213> ORGANISM: Homo sapien

<400> SEQUENCE: 4

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ala Cys Arg Ala Ser Gln Thr
        35                  40                  45

Ala Ser Arg Tyr Leu Ala Trp Tyr Gln Gln Lys Pro Gly Gln Ala Pro
    50                  55                  60

Arg Leu Leu Ile Tyr Asp Thr Ser Asn Arg Ala Thr Gly Ile Pro Ala
65                  70                  75                  80

Arg Phe Ser Gly Ser Gly Ser Gly Thr Asp Phe Thr Leu Ser Ile Ser
                85                  90                  95

Ser Leu Glu Pro Glu Asp Phe Ala Val Tyr Tyr Cys Gln Gln Arg Phe
            100                 105                 110

Asn Trp Pro Trp Thr Phe Gly Gln Gly Thr Lys Val Glu Phe Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 5
<211> LENGTH: 20
<212> TYPE: DNA
<213> ORGANISM: Homo sapien

<400> SEQUENCE: 5
accatggagt ttgggctgag                                               20

<210> SEQ ID NO 6
<211> LENGTH: 20
<212> TYPE: DNA
<213> ORGANISM: Homo sapien

<400> SEQUENCE: 6
actcatttac ccggggacag                                               20

<210> SEQ ID NO 7
<211> LENGTH: 20
<212> TYPE: DNA
<213> ORGANISM: Homo sapien

<400> SEQUENCE: 7
agcatggaag ccccagctca                                               20

<210> SEQ ID NO 8
<211> LENGTH: 21
<212> TYPE: DNA
<213> ORGANISM: Homo sapien

<400> SEQUENCE: 8
ctctaacact ctcccctgtt g                                             21
```

RABIES VIRUS-SPECIFIC NEUTRALIZING HUMAN MONOCLONAL ANTIBODIES AND NUCLEIC ACIDS AND RELATED METHODS

CROSS REFERENCE TO RELATED APPLICATIONS

This application claims priority under 35 U.S.C. §119 based upon U.S. Provisional Application No. 60/204,518, filed May 16, 2000.

FIELD OF THE INVENTION

The present invention relates to the fields of molecular biology and immunology and, more particularly, to the nucleic acid and amino acid sequence of human monoclonal rabies virus-neutralizing antibodies.

BACKGROUND OF THE INVENTION

Rabies is an acute, neurological disease caused by infection of the central nervous system with rabies virus, a member of the *Lyssavirus* genus of the family *Rhabdoviridae*. Of great historical significance due to its antiquity and the horrific nature of the disease, rabies virus continues to be an important threat of human and veterinary infection because of extensive reservoirs in diverse species of wildlife. Throughout much of the world, distinct variants of rabies virus are endemic in particular terrestrial animal species, with relatively little in common between them. While several islands, including the United Kingdom, Australia, Japan, and numerous islands are free of terrestrial rabies, rabies and rabies-related viruses associated with bats have recently been identified in the UK and Australia.

Rabies virus is characteristically bullet-shaped, enveloped particle of, on average, 75 by 180 nanometers. The virion consists of a single-stranded negative sense RNA genome and five structural proteins: the nucleoprotein (N) molecules, the phospho-protein (NS), the polymerase (L), the matrix protein (M) and the viral glycoprotein (G).

The N and G proteins both bear antigenic determinants which enable serotypic characterization of diverse rabies virus strains. N determinants are highly conserved between different virus isolates and are therefore very useful targets for the immunohistological detection of rabies virus infection using specific antibodies. On the other hand, antigenic determinants carried on the G-protein vary substantially among the rabies virus strains. Virus-neutralizing antibodies raised by vaccination with inactivated virus are directed against G. While it is clear that T cell responses to G, N, and NS, participate in immune responses to the virus under experimental conditions, assessment of immunity to rabies virus is generally limited to serology, particularly with respect to virus-neutralizing antibodies.

In areas of the world where human rabies is still common, the dog is the major reservoir of the viruses that infect man. Where canine rabies has largely been eliminated by vaccination, foxes, coyotes, skunks, raccoons, bats, and a variety of other mammals harbor variants of the virus. In many areas, wildlife reservoirs of virus continue to expand. Moreover, rabies virus can be transmitted from a reservoir species to humans or other end stage hosts by animals not normally associated with rabies, such as cats, rabbits, etc.

Almost invariably fatal once clinical symptoms appear, rabies can be averted by prompt treatment of an infected individual with a combination of passive and active immunization. Passive immunization consists of the administration of pre-formed rabies virus neutralizing antibodies obtained from pooled serum of rabies immune individuals (Human rabies-immune globulin; HRIG) or hyper-immunized horses (Equine rabies-immune globulin; ERIG). Both types of reagent present certain risks to recipients including variable antigen specificity, and thus potency, for different rabies virus isolates.

HRIG is prepared from pooled human sera, therefore there is the possibility that HRIG preparations could be contaminated with known or unknown human pathogens. On the other hand, as a preparation of foreign antigen, ERIG has been associated with severe anaphylactic reactions. Mouse monoclonals specific for rabies virus have been contemplated for use in post-exposure prophylaxis but, like ERIG, are antigenically foreign to humans. This may result in their rapid clearance from the human system, as well as the potential to cause an anaphylactic reaction.

To provide a better reagent, human monoclonal antibodies have been made by fusion of Epstein-Barr Virus (EBV)-transformed, rabies virus-specific human B cells with mouse-human heterohybrid donors. cDNA clones encoding the antibody heavy and light chains from these cells were constructed such that the antibodies were expressed in heterologous expression systems. These constructs allow rabies virus neutralizing human antibodies of defined specificity to be produced in a controlled system, purified away from possible deleterious contaminants. The present invention relates to these monoclonal rabies virus neutralizing human antibodies, the nucleic acid sequences of their heavy and light chains and the amino acid sequences of the encoded proteins. Also provided in the present invention are methods of using the monoclonal antibodies as a therapeutically effective post-exposure prophylactic treatment of individuals exposed to rabies virus.

SUMMARY OF THE INVENTION

It is an object of the present invention to isolate nucleic acid molecules having a heavy chain and a light chain nucleic acid sequence encoding a heavy chain and a light chain amino acid sequence. The heavy chain and light chain amino acid sequences are that of a monoclonal rabies virus neutralizing antibody that specifically binds to a rabies virus protein.

In one embodiment of the present invention that the isolated nucleic acid molecules that encode the monoclonal rabies virus neutralizing antibody are derived from cDNA sequences of the heavy chain SEQ. ID. NO: 1 and the light chain SEQ. ID. NO: 2.

It is an object of the present invention to provide an isolated human monoclonal rabies virus neutralizing antibody that is encoded in cDNA clones encoding the antibody heavy and light chains expressed in heterologous expression systems and purified away from deleterious contaminants. In one embodiment of the present invention the amino acid sequence of the isolated human monoclonal rabies virus neutralizing antibody is that of the SEQ. ID. NO: 3 and SEQ. ID. NO:4, respectively.

The present invention provides a fused gene encoding a chimeric immunoglobulin light chain. The chimeric light chain contains a first DNA sequence encoding an immunogloublin light chain variable region of a monoclonal rabies virus neutralizing antibody produced by a heterhybridoma cell line; and a second DNA sequence encoding a human light chain constant region. It is a further object of the present invention to provide an expression vector to express this fused gene. It is a further object to provide a host cell for the expression vector.

The present invention provides a fused gene encoding a chimeric immunoglobulin heavy chain. The chimeric heavy chain contains a first DNA sequence encoding an immunoglobulin heavy chain variable region of a monoclonal rabies virus neutralizing antibody produced by a heterhybridoma cell line; and a second DNA sequence encoding a human heavy chain constant region. It is a further object of the present invention to provide an expression vector to express this fused gene. It is a further object to provide a host cell for the expression vector.

It is another object of the present invention to provide an isolated monoclonal rabies virus neutralizing antibody derived from the fused gene encoding a chimeric immunoglobulin light chain and the fused gene encoding a chimeric immunoglobulin heavy chain.

It is an object of the present invention to provide a method of treating an individual exposed to a rabies virus by administering to the individual a therapeutically effective amount of a human monoclonal rabies virus neutralizing antibody that is encoded in cDNA clones encoding the antibody heavy and light chains expressed in heterologous expression systems and purified away from deleterious contaminants, thereby preventing the spread of the rabies virus to the central nervous system.

DESCRIPTION OF THE INVENTION

The present invention provides monoclonal antibodies that bind specifically to the glycoprotein of various rabies virus strains. Post-exposure treatment with monoclonal antibody, or a mixture of a variety of monoclonal antibodies, will neutralize the rabies virus at the site of entry and prevent the virus from spreading to the central nervous system (CNS). Thus, for transdermal or mucosal exposure to rabies virus, rabies specific-monoclonal antibodies are instilled into the bite site, as well as administered systemically. Since viral replication is restricted almost exclusively to neuronal cells, neutralization and clearance of the virus by the monoclonal antibodies of the present invention prior to entry into the CNS is an effective post-exposure prophylactic.

Cells

The human B cells used for hybridization were obtained from the peripheral blood of 5 donors between 7 and 21 days after the third dose of a primary rabies vaccination and 5 rabies-immune donors 10 to 21 days following administration of booster vaccine. In all cases the vaccine employed was Rabivac™ human diploid cell vaccine (virus strain Pitman Moore 1503-3M, Behringwerke, Marburg, FRG). All of the donors were negative in tests for HIV and hepatitis B. The mouse-human hybrid heteromyeloma SHM-D33 cells utilized as hybridoma fusion partners (Teng, N. N. et al, Proc. Natl. Acad. Sci. USA 80, 7308, 1983) and B95-8 Epstein-Barr Virus (EBV)-transformed marmoset leukocytes used as a source of EBV (Henderson et al., J. Exp. Med. Vol. 76, p. 152, 1977) were obtained from ATCC (Rockville, Md.).

Rabies Viruses

To assess the capacity of antibody preparations to neutralize a variety of rabies virus strains, a number of antigenically distinct fixed, laboratory strains, as well as two representative street rabies viruses, were used. Evelyn-Rokitnicki-Abelseth (ERA), challenge virus standard, either mouse brain adapted (CVS-24) or cell culture adapted (CVS-11), and Pitman-Moore (PM) fixed strains were obtained from the Thomas Jefferson University virus collection. Silver-haired bat rabies virus (SHBRV), which has been associated with most of the recent rabies cases in the United States of America, and coyote street rabies virus/ Mexican dog rabies virus (COSRV), which is a member of the dog rabies viruses, were obtained as described (Morimoto et al., Proc. Natl. Acad. Sci. USA, Vol 93, p. 5653, 1996). Virus purification and preparation of glycoprotein (G) and nucleoprotein (N) have been described elsewhere (Dietzschold et al., World Health Organization, Geneva, p. 175, 1996).

EBV-Transformation of Human PBLs

Peripheral blood mononuclear cells (PBMCs) were isolated from whole blood by density centrifugation on Ficoll-Paque (Amersham Pharmacia Biotech, Piscataway N.J.) as detailed elsewhere (Plebanski et al., Immunology Vol. 75, p. 86, 1992). T cells were then depleted by negative selection using monoclonal anti-CD2 antibody-coated magnetic beads (Dynal Inc., Lake Success N.Y.) and a magnetic particle concentrator (Dynal). CD-2-negative cells, primarily B cells, were collected and immortalized as previously described (Swaminathan, 1992). Briefly, B95-8 cells, cultured to confluency in $RPMI_{1640}$ (Gibco BRL Life Technologies, Grand Island N.Y.) supplemented with 10% fetal bovine serum (FBS; Gibco), were lysed by freeze-thawing on dry ice to release intracellular EBV. Supernatant containing EBV was clarified by spinning at 1000 RPM for 10 min and by filtration through a 0.45 μm filter. Virus was concentrated by centrifugation at 8000 RPM for 2 h at 4° C. $7 \times 10^6$ B cells (suspended in 1 ml of B95-8 culture media) were incubated at 37° C. for 2 h with virus prepared from 25 mls of B95-8 cells. Following infection, the cells were washed twice with culture media, plated in 96 well flat-bottom microtiter plates (Nunc, Fisher Scientific, Pittsburgh Pa.) at a concentration of $1 \times 10^4$ cells/well, and cultured at 37° C. in a humidified atmosphere of 5% $CO_2$ and 95% air.

Establishment of Mouse-Human Heterohybrids

After the EBV-transformed cell lines had been cultured for approximately 4 weeks, supernatant was harvested and tested for the presence of rabies virus-specific antibody in ELISA. Positive wells were transferred first to 1 ml and then to 2 ml cultures (48 and 24 well plates, Nunc) and the supernatant then assayed in the rapid fluorescent focus inhibition test (RFFIT) for rabies virus neutralizing antibody, as detailed elsewhere (Hooper, ASM Press, WA p. 755, 1997). Cell lines producing neutralizing antibody were hybridized with SHM-D33 cells (ATCC Accession Number CRL1668) as follows. Equal numbers of SHM-D33 and EBV-transformed cells (approximately $5 \times 10^6$ each) were added together into a sterile polystyrene round-bottom tube (Falcon, Fisher Scientific) and centrifuged at 1000 RPM for 10 min. Cells were washed twice with serum-free medium and the cell pellet resuspended in 100 μl of medium.

Tubes were warmed in a 37° C. water bath for 1 min and then 0.5 ml of warm (37° C.) 50% (wt/vol) polyethylene glycol (Sigma Chemical Co., St. Louis Mo., cat. #P-7181) was added, dropwise over a 45-sec period while gently shaking the tube. The fusion reaction was then stopped by the slow addition of 3 ml of serum-free medium over 30 sec followed by the addition of 9 ml over 30 sec. The tubes were allowed to stand at room temperature for 8 min and then incubated for 2 min in a 37° C. water bath. The cells were then centrifuged at 500 g for 3 min and the cell pellet gently resuspended in 30 ml of Iscove's modification of Dulbecco's (IMDM; Gibco) medium containing 10% FBS, as well as 0.04 μM aminopterin (Gibco) and 10 μM oubain (Sigma) to select against cells which had not hybridized. Cell suspensions were plated in 96 well flat-bottom microtiter plates at a concentration of $1 \times 10^4$ cells per well and incubated as described for the lines.

When colonies of heterohybrid cells had become established (approximately 6 weeks of culture) supernatants were tested for rabies virus-specific antibody production in ELISA and RFFIT. Antibody-producing cells were cloned a minimum of three times by limiting dilution in microtiter plates. Cells were titrated in 96 well round bottom plates in 2-fold dilutions starting from 4 cells per well. Cells from wells containing an average of 0.25 cells or less were expanded for the collection of supernatant and further analysis.

Analysis of Rabies Virus-Specific Antibodies in ELISA

Antibody specificity and isotype was assessed in solid phase ELISA. Plates (PolySorb™, Nunc) were coated at room temperature in a humidified chamber overnight with 5·g/ml rabies ERA virus, glycoprotein, or nucleoprotein diluted in phosphate-buffered saline (PBS). The plates were then blocked with 5% powdered milk in PBS and washed in PBS containing 0.05% Tween$_{20}$ (PBS-Tween) prior to the addition of supernatant samples.

Following incubation at room temperature for 2 h, the plates were washed with PBS-Tween to remove unbound primary antibody and various enzyme-conjugated or biotinylated secondary antibodies specific for the various human heavy chain isotypes were added for 1 h at room temperature. Secondary antibody was detected either by the production of a soluble end product in the medium upon addition of the appropriate substrate (3,3',5,5'-tetramethylbenzidine (TMB) in phosphate-citrate buffer, or p-nitrophenyl phosphate (PNPP) in 0.1M glycine buffer, Sigma) or following the addition of avidin-alkaline phosphatase (30 min at RT) and PNPP substrate. The peroxidase-TMB reaction was stopped by the addition of 2M $H_2SO_4$. Absorbance values were read in a microplate spectrophotometer (Biotek, Winooski Vt.) at 450 nm for the TMB product and at 405 nm for the PNPP reaction.

RFFIT

Supernatant samples from each transformed cell line were assayed for the presence of rabies virus-neutralizing antibodies using a variation of the rapid fluorescent focus inhibition test (RFFIT) as previously described (Hooper, *ASM Press*, WA p. 755, 1997). Supernatant samples (50 µl) were diluted in 96 well flat-bottom plates (Nunc). 30 µl of a rabies virus dilution known to cause 80–90% infection of the indicator cells were added to each test sample, and the plates incubated at 37° C. for 1 h. Negative media and positive rabies-immune serum control samples were included in each assay. After incubation, 30 µl of a $1.8 \times 10^6$ cells/ml concentration of baby hamster kidney (BHK) cells were added to each well and the cultures incubated overnight at 37° C. The plates were then washed once with ice-cold PBS and fixed with ice-cold 90% acetone for 20 min at −20° C. After fixation, acetone was removed and the plates were air dried. To detect infected BHK cells, 40 µl of FITC anti-rabies nucleoprotein monoclonal globulin (Centocor, Malvern Pa.) were added to each well for 45 min at 37° C. The plates were then washed three times with distilled water and examined under a fluorescent microscope.

Purification of Antibodies by Affinity Chromatography

IgG1 antibody was purified using a protein A column (rProtein A Sepharose™ Fast Flow, Amersham Pharmacia Biotech). Briefly, supernatants were clarified by filtration through a 0.45 µm membrane and the pH adjusted to 8.0 with 1N NaOH. Supernatant was run through the column at a linear flow rate of approximately 100 cm/hour. After washing in PBS (pH 8), antibody was eluted from the column using a 0.1M citric acid solution and then dialyzed against PBS.

IgG3 antibody was purified using a protein G column (Protein G Sepharose™ Fast Flow, Amersham Pharmacia Biotech). IgG3-containing supernatant was clarified by filtration through a 0.45 µm membrane and the pH adjusted to 7.0 with 1N NaOH. Supernatant was run through the column at a linear flow rate of approximately 11 cm/hour. After washing with PBS, antibody was eluted from the column using 0.1M glycine buffer, pH 3.0, and then dialyzed against PBS.

IgM antibody was purified using mannan binding protein and a modification of a previously described technique (Nevens et al., *J. Chromatogr*, Vol. 597, p. 247, 1992). Briefly, supernatant containing IgM was EDTA treated, brought to pH 8.0 with 1M NaOH, filtered and cooled to 4° C. Mannan binding protein-agarose (Sigma) was washed in a column at 4° C. with binding buffer consisting of 0.1M $NaHCO_3$/0.5M NaCl, pH 8.3 and then the supernatant was added and incubated on the column for 15 min at 4° C. The column was then washed with several volumes of binding buffer and brought to RT for 1 h. The IgM was eluted from the column with binding buffer at RT and dialyzed against PBS.

Protein concentrations of the dialyzed antibody preparations were determined using a protein detection assay (Bio-Rad Laboratories, Hercules Calif.) as follows. 100 µl of sample were added to 5 ml of a ⅕ dilution of dye reagent concentrate and incubated at RT for 10 minutes. Negative PBS control and various bovine serum albumin (BSA) protein standards were included in each assay. After incubation, samples were read in a spectrophotometer at 595 nm. Protein concentrations of test samples were calculated with reference to the absorbance of the BSA standards. The purity of all antibody preparations was assessed by electrophoresis in 12.5% polyacrylamide gel under reducing conditions (SDS-PAGE). Purified antibodies showed two major bands on SDS-PAGE corresponding to isolated heavy and light immunoglobulin chains.

Generation, Isolation and Sequencing of cDNA Clones

Total RNA was isolated from JA hybridoma cell by using RNAzol B (Biotecx Laboratories, Houston). Reverse transcriptase reactions were performed at 42° C. for 1 hr with avian myeloblastosis virus reverse transcriptase (Promega) and oligo(dT) primer. A portion of the reverse transcriptase products were subjected to polymerase chain reaction (PCR) amplification using heavy chain specific primers: IgG-HF1 primer (5'-ACC<u>ATG</u>GAGTTTGGGCTGAG-3' (SEQ. ID. NO: 5), start codon; underline, accession #Y14737), and IgG-HR2 primer (5'-AC<u>TCA</u>TTTACCCGGGGACAG-3' (SEQ. ID. NO: 6), stop codon; underline, accession #Y14737) or light chain specific primers: IgG-LF5 primer (5'-AGC<u>ATG</u>GAAGCCCCAGCTCA-3' (SEQ. ID. NO: 7), start codon; underline, accession #M63438), and IgG-LR2 primer (5'-CT<u>CTA</u>ACACTCTCCCCTGTTG-3' (SEQ. ID. NO: 8), stop codon; underline, accession #M63438). Amplification was carried out for 35 cycles of denaturation at 94° C. for 60 seconds, annealing at 50° C. for 60 seconds, and polymerization at 72° C. for 90 seconds with Taq DNA polymerase (Promega). The PCR products (1.4 kb for heavy chain, 0.7 kb for light chain) were purified and sequenced by using the AmpliTaq cycle sequencing kit (Perkin-Elmer) with the specific primers. The PCR products were cloned into TA cloning vector, pCR2.1 (Invitrogen). The cloned heavy chain and light chain cDNA was sequenced by using the AmpliTaq cycle sequencing kit (Perkin-Elmer) with the specific primers.

Monoclonal Rabies Virus Neutralizing Antibody Coding Sequences

Monoclonal antibody cDNA, and sequences complementary thereto, are monoclonal antibody nucleic acids provided by the present invention. In a specific embodiment herein, a monoclonal antibody cDNA sequence is provided for the heavy chain (SEQ. ID. NO: 1) and the light chain (SEQ. ID. NO: 2) of the monoclonal antibody from clone JA, thus lacking any introns.

The invention also provides single-stranded oligonucleotides for use as primers in PCR that amplify a monoclonal antibody sequence-containing fragment, for example the variable or hypervariable region of the monoclonal antibody. The oligonucleotide having the sequence of a hybridizable portion, at least 8 nucleotides, of a monoclonal antibody gene, and another oligonucleotide having the reverse complement of a downstream sequence in the same strand of the monoclonal antibody gene, such that each oligonucleotide primes synthesis in a direction toward the other. The oligonucleotides are preferably in the range of 10–35 nucleotides in length.

The present invention provides the full-length cDNA sequences for the heavy and light chains of the monoclonal antibody of heterohybridoma clone JA (SEQ ID NO: 1 and SEQ ID NO: 2, respectively), and the encoded polypeptides of #1-474 amino acids for the heavy chain (SEQ ID NO: 3) and #1-234 amino acids for the light chain (SEQ. ID. NO:4).

In a specific embodiment disclosed herein, the invention relates to the nucleic acid sequence of the monoclonal antibody from heterohybridoma clone JA. In a preferred, but not limiting, aspect of the invention; the heterohybridoma clone JA is the source of the monoclonal antibody cDNA.

Functional Equivalents of Monoclonal Rabies Virus Neutralizing Antibodies

The invention also includes functional equivalents of the antibodies described in this specification. Functional equivalents have binding characteristics comparable to those of the antibodies, and include, for example, chimerized and single chain antibodies, as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424.

Functional equivalents include polypeptides with amino acid sequences substantially the same as the amino acid sequence of the variable or hypervariable regions of the antibodies of the present invention. "Substantially the same" amino acid sequence is defined herein as a sequence with at least 70%, preferably at least about 80%, and more preferably at least about 90% homology to another amino acid sequence, as determined by the FASTA search method in accordance with Pearson and Lipman, *Proc. Natl. Inst. Acad. Sci. USA* 85, 2444–2448, 1988. Chimerized antibodies have constant regions derived substantially or exclusively from human antibody constant regions and variable regions derived substantially or exclusively from the sequence of the variable region of a monoclonal antibody from each stable heterohybridoma (Champion, J. M., et al., *Journal of Immunological Methods*, 235 81–90, 2000).

Single chain antibodies or Fv fragments are polypeptides that consist of the variable region of the heavy chain of the antibody linked to the variable region of the light chain, with or without an interconnecting linker. Thus, the Fv comprises the entire antibody combining site.

Functional equivalents further include fragments of antibodies that have the same, or substantially the same, binding characteristics to those of the whole antibody. Such fragments may contain one or both Fab fragments or the F(ab').sub.2 fragment. Preferably the antibody fragments contain all six complement determining regions of the whole antibody, although fragments containing fewer than all of such regions, such as three, four or five complement determining regions, are also functional. The functional equivalents are members of the IgG immunolglobulin class and subclasses thereof, but may be or may combine any one of the following immunoglobulin classes: IgM, IgA, IgD, or IgE, and subclasses thereof. Heavy chains of various subclasses, such as the IgG subclasses, are responsible for different effector functions and thus, by choosing the desired heavy chain constant region, chimeric antibodies with desired effector function are produced. Preferred constant regions are gamma 1 (IgG1), gamma 3 (IgG3) and gamma 4 (IgG4). The light chain constant region can be of the kappa or lambda type.

The immunoglobulins of the present invention can be monovalent, divalent or polyvalent. Monovalent immunoglobulins are dimers (HL) formed of a chimeric heavy chain associated through disulfide bridges with a chimeric light chain. Divalent immunoglobulins are tetramers (H.sub.2 L.sub.2) formed of two dimers associated through at least one disulfide bridge.

Standard Recombinant DNA Techniques

Standard recombinant DNA techniques are described in Sambrook et al., "Molecular Cloning," Second Edition, Cold Spring Harbor Laboratory Press (1987) and by Ausubel et al.(Eds) "Current Protocols in Molecular Biology," Green Publishing Associates/Wiley-Interscience, New York (1990).

Briefly, a suitable source of cells containing nucleic acid molecules that express the desired DNA, such as an antibody or antibody equivalent, is selected. Total RNA is prepared by standard procedures from a suitable source. The total RNA is used to direct cDNA synthesis. Standard methods for isolating RNA and synthesizing cDNA are provided in standard manuals of molecular biology such as, for example, those described above.

The cDNA may be amplified by known methods. For example, the cDNA may be used as a template for amplification by polymerase chain reaction (PCR); see Saiki et al., *Science*, 239, 487, 1988 or Mullis et al., U.S. Pat. No. 4,683,195. The sequences of the oligonucleotide primers for the PCR amplification are derived from the known sequence to be amplified. The oligonucleotides are synthesized by methods known in the art. Suitable methods include those described by Caruthers in *Science* 230, 281–285, 1985.

A mixture of upstream and downstream oligonucleotides are used in the PCR amplification. The conditions are optimized for each particular primer pair according to standard procedures. The PCR product is analyzed, for example, by electrophoresis for cDNA having the correct size, corresponding to the sequence between the primers.

Alternatively, the coding region may be amplified in two or more overlapping fragments. The overlapping fragments are designed to include a restriction site permitting the assembly of the intact cDNA from the fragments.

In order to isolate the entire protein-coding regions for the heavy and light chains of each monoclonal antibody from each heterohybridoma cell line, for example, the upstream PCR oligonucleotide primer is complementary to the sequence at the 5' end, encompassing the ATG start codon and at least 5–10 nucleotides upstream of the start codon. The downstream PCR oligonucleotide primer is complementary to the sequence at the 3' end of the desired DNA sequence. The desired cDNA sequence encodes the entire portion of the heavy and light chains of each monoclonal antibody, including the stop codon.

The cDNA to be amplified, such as that encoding antibodies or antibody equivalents, may also be replicated in a wide variety of cloning vectors in a wide variety of host cells. The host cell may be prokaryotic or eukaryotic.

The vector into which the monoclonal antibody cDNA is spliced may comprise segments of chromosomal, non-chromosomal and synthetic DNA sequences. Some suitable prokaryotic cloning vectors include, but are not limited to, plasmids from *E. coli*, such as colE1, pCR1, pBR322, pMB9, pUC, pKSM, and RP4. Prokaryotic vectors also include, but are not limited to, derivatives of phage DNA such as M13 and other filamentous single-stranded DNA phages.

The vector containing the monoclonal antibody cDNA to be expressed is transfected into a suitable host cell, as described infra. The host cell is maintained in an appropriate culture medium, and subjected to conditions under which the cells and the vector replicate.

Chimeric Antibodies

In general, the chimeric antibodies are produced by preparing, for each of the light and heavy chain components of the chimeric immunoglobulin, a fused gene comprising a first DNA segment that encodes at least the functional portion of the human rabies virus specific neutralizing, preferably glycoprotein, human variable region linked (e.g., functionally rearranged variable region with joining segment) to a second DNA segment encoding at least a part of a human constant region. Each fused gene is assembled in or inserted into an expression vector. Recipient cells capable of expressing the gene products are then transfected with the genes. The transfected recipient cells are cultured under conditions that permit expression of the incorporated genes and the expressed immunoglobulins or immunoglobulin chains are recovered.

Genes encoding the variable region of immunoglobulin heavy and light chains are obtained from lymphoid cells that produce the monoclonal rabies virus neutralizing antibodies. For example, the heterohybridoma cell lines that produce monoclonal antibody against the rabies glycoprotein provide a source of immunoglobulin variable region for the present chimeric antibodies. Constant regions are obtained from human antibody-producing cells by standard cloning techniques. Alternatively, because genes representing the two classes of light chains and the five classes of heavy chains have been cloned, constant regions of human origin are readily available from these clones. Chimeric antibody binding fragments such as F(ab').sub.2 and Fab fragments are prepared by designing a chimeric heavy chain gene in truncated form. For example, a chimeric gene encoding a F(ab').sub.2 heavy chain portion would include DNA sequences encoding the CH.sub.1 domain and hinge region of the heavy chain. Alternatively, such fragments can be obtained by enzymatic cleavage of a chimeric immunoglobulin. For instance, papain or pepsin cleavage can generate Fab or F(ab').sub.2 fragments, respectively.

Preferably, the fused genes encoding the heavy and light chimeric chains, or portions thereof, are assembled in two different expression vectors that can be used to cotransfect a recipient cell. Each vector contains two selectable genes, one for selection in a bacterial system and one for selection in a eukaryotic system, each vector having a different pair of genes. These vectors allow production and amplification of the fused genes in bacterial systems, and subsequent cotransfection of eukaryotic cells and selection of the cotransfected cells. Examples of selectable genes for the bacterial system include, but are not limited to, the genes that confer ampicillin resistance and the gene that confers chloramphenicol resistance. Two selectable genes for selection of eukarytoic transfectants are preferred, but are not limited to: (i) the xanthine-guanine phosphoribosyltransferase gene (gpt), and (ii) the phosphotransferase gene from Tn5 (designated neo). Selection with gpt is based on the ability of the enzyme encoded by this gene to use xanthine as a substrate for purine nucleotide synthesis; the analogous endogenous enzyme cannot. In a medium containing xanthine and mycophenolic acid, which blocks the conversion of inosine monophosphate to xanthine monophosphate, only cells expressing the gpt gene can survive. The product of the neo blocks the inhibition of protein synthesis in eukarytoic cells caused by the antibiotic G418 and other antibiotics of its class. The two selection procedures can be used simultaneously or sequentially to select for the expression of immunoglobulin chain genes introduced on two different DNA vectors into a eukaryotic cell.

Expression Systems

Due to the inherent degeneracy of the genetic code, other DNA sequences which encode substantially the same or a functionally equivalent heavy and light chain amino acid sequences, is within the scope of the invention. Altered DNA sequences which may be used in accordance with the invention include deletions, additions or substitutions of different nucleotide residues resulting in a sequence that encodes the same, or a functionally equivalent, gene product. The gene product itself may contain deletions, additions or substitutions of amino acid residues within a heavy or light chain sequence which result in a silent change, thus producing a functionally equivalent monoclonal antibody.

In accordance with the present invention, nucleotide sequences coding for heavy and light chains of the monoclonal rabies virus neutralizing antibody, a fragment or analog thereof, are inserted into an appropriate expression vector. This vector which contains the necessary elements for transcription and translation of the inserted protein-coding sequence so as to generate recombinant DNA molecules that direct the expression of heavy and light chain immunoglobulins for the formation of monoclonal rabies virus neutralizing antibody.

The preferred recipient cell line is a myeloma cell. Myeloma cells can synthesize, assemble and secrete immunoglobulins encoded by transfected immunoglobulin genes. Further, they possess the mechanism for glycosylation of the immunoglobulin. A particularly preferred recipient cell is a myeloma cell line that does not produce immunoglobulin, such as Sp2/0. These cell lines produce only the immunoglobulin encoded by the transfected immunoglobulin genes. Myeloma cells can be grown in culture or in the peritoneum of mice where secreted immunoglobulin can be obtained from ascites fluid. Other lymphoid cells such as B lymphocytes or hybridoma cells can serve as suitable recipient cells.

Several methods exist for transfecting lymphoid cells with vectors containing immunoglobulin encoding genes. A preferred way of introducing DNA into lymphoid cells is by electroporation. In this procedure recipient cells are subjected to an electric pulse in the presence of the DNA to be incorporated. Another way to introduce DNA is by protoplast fusion. In this method, lysozyme is used to strip cell walls from bacteria harboring the recombinant plasmid containing the immunoglobulin gene. The resulting spheroplasts are fused with myeloma cells with polyethylene glycol. After protoplast fusion, the transfectants are selected and isolated. Another technique that can be used to introduce DNA into many cell types is calcium phosphate precipitation.

The immunoglobulin genes can also be expressed in nonlymphoid cells, such as bacteria or yeast. When expressed in bacteria, the immunoglobulin heavy chains and light chains become part of inclusion bodies. Thus, the chains must be isolated and purified and then assembled into functional immunoglobulin molecules. Other strategies for expression in *E. coli* are available (see e.g., Pluckthun, A., *BioTechnology* 9:545–551, 1991; Skerra, A. et al., *BioTechnology* 9:273–278, 1991), including secretion from *E. coli* as fusion proteins comprising a signal sequence.

---

What is claimed is:

1. An isolated human monoclonal rabies virus-neutralizing antibody comprising a heavy chain polypeptide comprising an amino acid sequence having at least 80% amino acid sequence identity to SEQ ID NO:3 and a light chain polypeptide comprising an amino acid sequence having at least 80% amino acid sequence identity to SEQ ID NO:4.

2. The antibody according to claim 1 comprising a heavy chain polypeptide comprising an amino acid sequence having at least 90% amino acid sequence identity to SEQ ID NO:3 and a light chain polypeptide comprising an amino acid sequence having at least 90% amino acid sequence identity to SEQ ID NO:4.

3. An isolated human monoclonal rabies virus-neutralizing antibody comprising a heavy chain polypeptide having the amino acid sequence SEQ ID NO:3 and a light chain polypeptide having the amino acid sequence SEQ ID NO:4.

* * * * *